United States Patent
Serhan et al.

(10) Patent No.: US 9,327,015 B2
(45) Date of Patent: May 3, 2016

(54) METHODS AND DEVICES FOR CORRECTING SPINAL DEFORMITY WITH PHARMACEUTICAL-ELUTING PEDICLE SCREWS

(75) Inventors: Hassan Serhan, Raynham, MA (US); Michael J. O'Neil, Raynham, MA (US); Sean Lilienfeld, Raynham, MA (US); Thomas M. DiMauro, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 719 days.

(21) Appl. No.: 12/730,469

(22) Filed: Mar. 24, 2010

(65) Prior Publication Data

US 2011/0097377 A1    Apr. 28, 2011

Related U.S. Application Data

(63) Continuation-in-part of application No. 12/605,122, filed on Oct. 23, 2009.

(51) Int. Cl.
| | |
|---|---|
| *A61K 31/65* | (2006.01) |
| *A61B 17/58* | (2006.01) |
| *A61B 17/70* | (2006.01) |
| *A61K 38/30* | (2006.01) |
| *A61K 38/18* | (2006.01) |
| *A61B 17/86* | (2006.01) |
| *A61B 17/00* | (2006.01) |
| *A61B 17/56* | (2006.01) |

(52) U.S. Cl.
CPC ............ *A61K 38/30* (2013.01); *A61B 17/7061* (2013.01); *A61K 31/65* (2013.01); *A61K 38/1875* (2013.01); *A61B 17/7098* (2013.01); *A61B 17/864* (2013.01); *A61B 2017/00893* (2013.01); *A61B 2017/561* (2013.01)

(58) Field of Classification Search
None
See application file for complete search history.

(56) References Cited

U.S. PATENT DOCUMENTS

| | | | |
|---|---|---|---|
| 5,270,300 A | 12/1993 | Hunziker | |
| 5,728,396 A | 3/1998 | Peery | |
| 6,049,026 A | 4/2000 | Muschler | |
| 6,277,969 B1 | 8/2001 | Le | |
| 2004/0063674 A1* | 4/2004 | Levy et al. | 514/152 |
| 2005/0112091 A1* | 5/2005 | DiMauro et al. | 424/85.1 |
| 2007/0250045 A1* | 10/2007 | Trieu | 604/890.1 |

FOREIGN PATENT DOCUMENTS

WO    WO 03000190    1/2003

OTHER PUBLICATIONS

Aebi, M., Eur. Spine J., 2005, vol. 14:925-948.*

(Continued)

*Primary Examiner* — Xiaozhen Xie

(57) ABSTRACT

A method of correcting spinal deformity, which includes locating pharmaceutical-loaded implants adjacent to targeted spinal growth plates, and then eluting the pharmaceutical onto the growth plates. Preferably, the method involves correcting spinal deformity by simply inserting a pharmaceutical-eluting pedicle screw onto the concave side of a scoliotic curve. In some embodiments, the screw has a cannulated internal reservoir that contains a growth-inhibiting pharmaceutical (such as a tetracycline) and at least one fenestration that allows the pharmaceutical to elute onto the vertebral body growth plate.

22 Claims, 6 Drawing Sheets

(56) References Cited

OTHER PUBLICATIONS

Ballock, "Physiology and pathophysiology of the growth plate", *Birth Defects Res Part C Embryo Today*, 2003; pp. 123-143, vol. 69(2).
Van Der Eerden, "Systemic and local regulation of the growth plate", *Endocr Rev.*, 2003, pp. 782-801, vol. 24(6).
Kronenberg, "Developmental regulation of the growth plate. Systemic and local regulation of the growth plate", *Nature*, May 15, 2003, pp. 332-336, vol. 423(6937).
Rabie, "Regulates chondrocyte maturation in condylar cartilage", *J Dent Res.*, 2003;82(8):627-31.
Schipani, "Receptor in endochondral bone development", *Birth Defects Res Part C Embryo Today*, 2003;pp. 352-362, vol. 69(4).
Serra, "Parathyroid hormone-related peptide (PTHrP)-dependent and -independent effects of transforming growth factor beta (TGF-beta) on endochondral bone formation", *J. Cell Biol.*, 1999;pp. 783-794, vol. 145(4).
Yakar, "Circulating levels of IGF-1 directly regulate bone growth and density", *J Clin Invest.* 2002;pp. 771-781, vol. 110(6).
Mark, "Hydrogels", *Concise Encyclopedia of Polymer Science and Engineering*, 1990, pp. 458-459, Wiley and Sons.
Cohlan, "Growth Inhibition of Prematures Receiving Tetracycline", *Am. J. Dis. Child.*, 1963, vol. 105, p. 453.
Demers, "Effects of tetracyclines on skeletal growth dentition: A report by the nutrition committee of the Canadian Paediatric Society", *Can. Med. Assn. J.*, vol. 99, Nov. 2, 1968, pp. 849-854.
Simmons, "The effect of protracted tetracycline treatment on bone growth and maturation", *Clin. Orthop. Rel. Res.*, Nov. 1983;pp. 253-259, (180)—abstract.

\* cited by examiner

METHODS AND DEVICES FOR CORRECTING SPINAL DEFORMITY WITH PHARMACEUTICAL-ELUTING PEDICLE SCREWS

CONTINUING DATA

This application is a continuation-in-part of and claims priority from co-pending U.S. Ser. No. 12/605,122, entitled "Method and Devices for Correcting Spinal Deformity with Pharmaceutical-Eluting Pedicle Screws" (Serhan), filed Oct. 23, 2009

BACKGROUND OF THE INVENTION

Surgical correction of spinal deformities such as scoliosis typically requires fusion of several spinal motion segments. Although this procedure corrects the deformity, it is highly invasive and also severely reduces the flexibility of the spine. Vertebral body tethering or stapling are alternatives that can preserve spinal motion, but require highly invasive surgical procedures in order to achieve the desired correction.

State of the art devices for correction of spinal deformities typically include large assemblies of bone screws connected by cylindrical rods that are implanted posteriorly through the pedicles, or anteriorly on the lateral aspect of the vertebral bodies. Newer correction systems include interconnecting elements between the rod and the screw that allow relative motion between the rod and the screw, effectively allowing the spine to grow without removing the implants. However, the more recent motion-preserving designs are not appropriate for patients who have reached skeletal maturity. Staple and tether systems have been described for mechanically halting progression of the spinal deformity on the concave side of the curve. Several prosthetic disc devices have been described for replacing a diseased intervertebral disc, but these are not designed to correct spinal deformity. Therefore, there is a need for a minimally invasive spinal deformity correction system.

Bone growth during childhood and adolescence requires the coordinated and continuous proliferation and differentiation of chondrocytes in the growth plate. Sandwiched between the primary and secondary centers of ossification of bones, the growth plates are polarized, with resting cells nearest the epiphyseal bone, a zone of proliferation, a zone of hypertrophy and differentiation, and a zone of apoptosis where the cartilage cells die and are replaced by osteoblasts. (Ballock R T, O'Keefe R J. Physiology and pathophysiology of the growth plate. *Birth Defects Res Part C Embryo Today* 2003; 69(2):123-43.) The continuous passage of new chondrocytes from the resting zone through these strata is responsible for longitudinal bone growth (van der Eerden B C, Karperien M, Wit J M. Systemic and local regulation of the growth plate. *Endocr Rev.* 2003; 24(6):782-801. Kronenberg H M, Developmental regulation of the growth plate. Systemic and local regulation of the growth plate. *Nature* 2003 May 15; 423(6937):332-6. Rabie A B, Tang G H, Xiong H, Hagg U. PTHrP regulates chondrocyte maturation in condylar cartilage. *J Dent Res.*, 2003; 82(8):627-31. Schipani E, Provot S. PTHrP, PTH, and the PTH/PTHrP receptor in endochondral bone development. *Birth Defects Res Part C Embryo Today*, 2003; 69(4):352-62). Defects in coordinated and continuous proliferation and differentiation of chondrocytes may cause serious skeletal disorders such as scoliosis, where growth becomes asymmetric, resulting in deformities in the spine.

There have been several articles describing the use of growth factors (including BMPs) to initiate bony growth at desired locations. While BMP's stimulate Indian hedgehog (Ihh) production, thus stimulating bone growth (Serra R, Karaplis A, Sohn P. Parathyroid hormone-related peptide (PTHrP)-dependent and -independent effects of transforming growth factor beta (TGF-beta) on endochondral bone formation. *J. Cell Biol* 1999; 145(4):783-94. Yakar S, Rosen C J, Beamer W G, Ackert-Bicknell C L, Wu Y, Liu J L, et al. Circulating levels of IGF-1 directly regulate bone growth and density. *J Clin Invest.* 2002; 110(6):771-81), it is assumed that the local signaling pathways are acted upon by systemic factors, including growth hormone (GH), insulin-like growth factors (IGF's), androgens, estrogens, thyroid hormones, which control overall rates of bone growth. (Schipani E, Provot S. PTHrP, PTH, and the PTH/PTHrP receptor in endochondral bone development. *Birth Defects Res Part C Embryo Today* 2003; 69(4):352-62).

SUMMARY OF THE INVENTION

The present invention relates to a method of correcting a spinal deformity (and scoliosis in particular), comprising the steps of a) locating a pharmaceutical-loaded implant adjacent to a targeted spinal growth plate in a patient having the spinal deformity, and b) eluting an effective amount of the pharmaceutical onto the targeted spinal growth plate.

Preferably, the present invention comprises a method and device for correcting spinal deformity, which includes simply inserting a pharmaceutical-eluting pedicle screw onto the concave side of a scoliotic curve. The screw has a cannulated internal reservoir that contains a chondrocyte growth-inducing pharmaceutical (such as a growth factor or small molecule) and at least one fenestration that allows the pharmaceutical to elute onto the vertebral body growth plate. This method aims to control the longitudinal growth of the target vertebral bodies during childhood and adolescence by allowing coordinated and continuous proliferation and differentiation of chondrocytes in the growth plate.

Therefore, in accordance with the present invention, there is provided a method of correcting spinal deformity comprising the steps of:
 a) locating a pharmaceutical-loaded implant adjacent to a targeted spinal growth plate in a patient having a spinal deformity, and
 b) eluting the pharmaceutical onto the growth plate (preferably on a concave side of the deformity) in an amount effective to cause cartilage growth (and/or bone formation) in the targeted spinal growth plate.

DETAILED DESCRIPTION OF THE INVENTION

For the purposes of the present invention, a bone screw may be threaded or unthreaded. Preferably, the bone screw is threaded. However, in some embodiments, the bone screw may be unthreaded. Preferably, the bone screw has a proximal head having a polyaxial connection means for connection to a spinal rod. However, in some embodiments, the bone screw may not have a proximal head. A "chondrogenic agent" (or "CG agent") is either a pharmaceutical that augments the proliferation and/or differentiation of chondrocytes, or a stem cell that has the capacity to differentiate into a chondrocyte. A "growth plate" is often identified herein as a "GP".

In some embodiments of the present invention, the pharmaceutical—loaded screws are inserted into at least one of the vertebral bodies that are adjacent to the targeted growth plate. The screws are placed into the bone (typically through a pedicle) in a location adjacent the concave portion of the targeted scoliotic region.

Figure 1A:
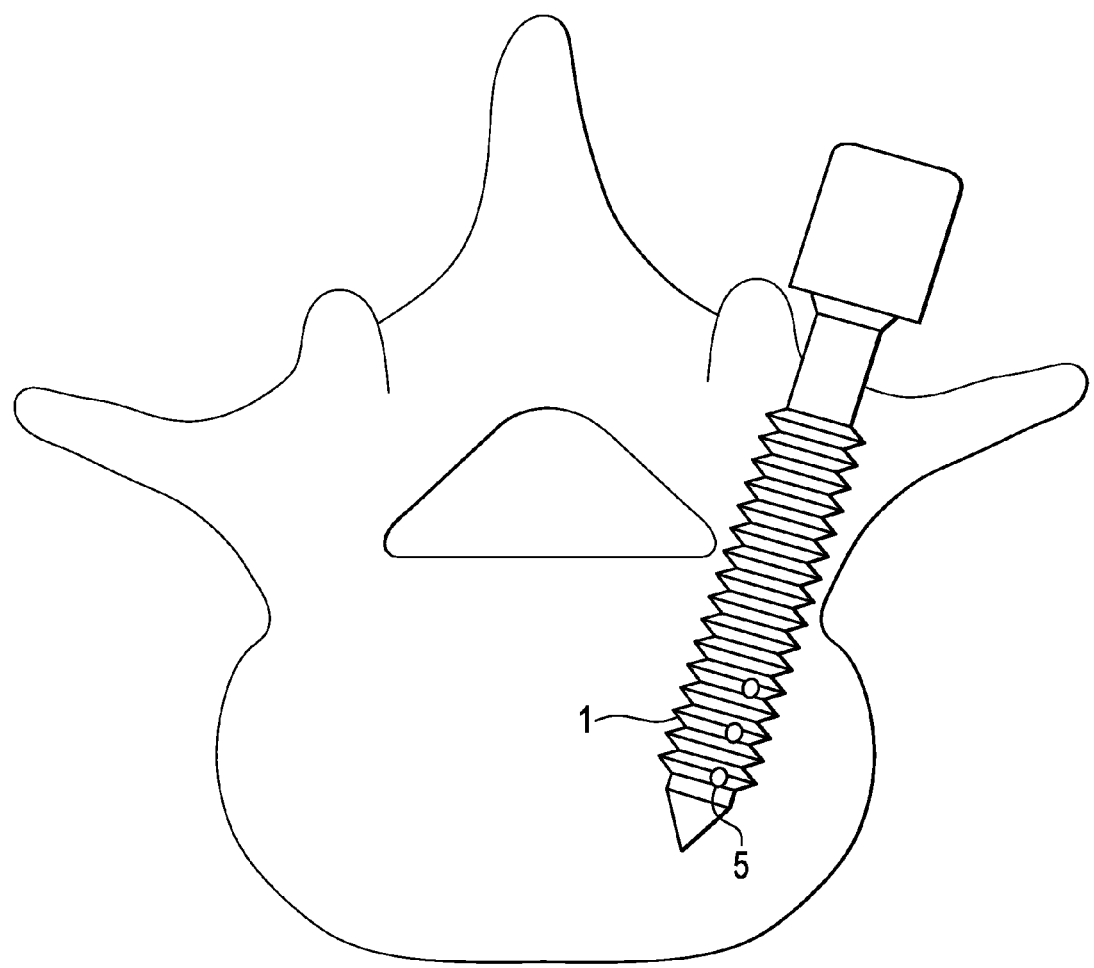
FIG. 1a is a cross-section of a human vertebra having a device of the present invention implanted therein, wherein the device traverse a pedicle.

FIG. 1a is a cross-section of a human vertebra having a device 1 of the present invention implanted through a pedicle, wherein the device has fenestrations 5 for eluting the pharmaceutical contained therein.

Figure 1B:
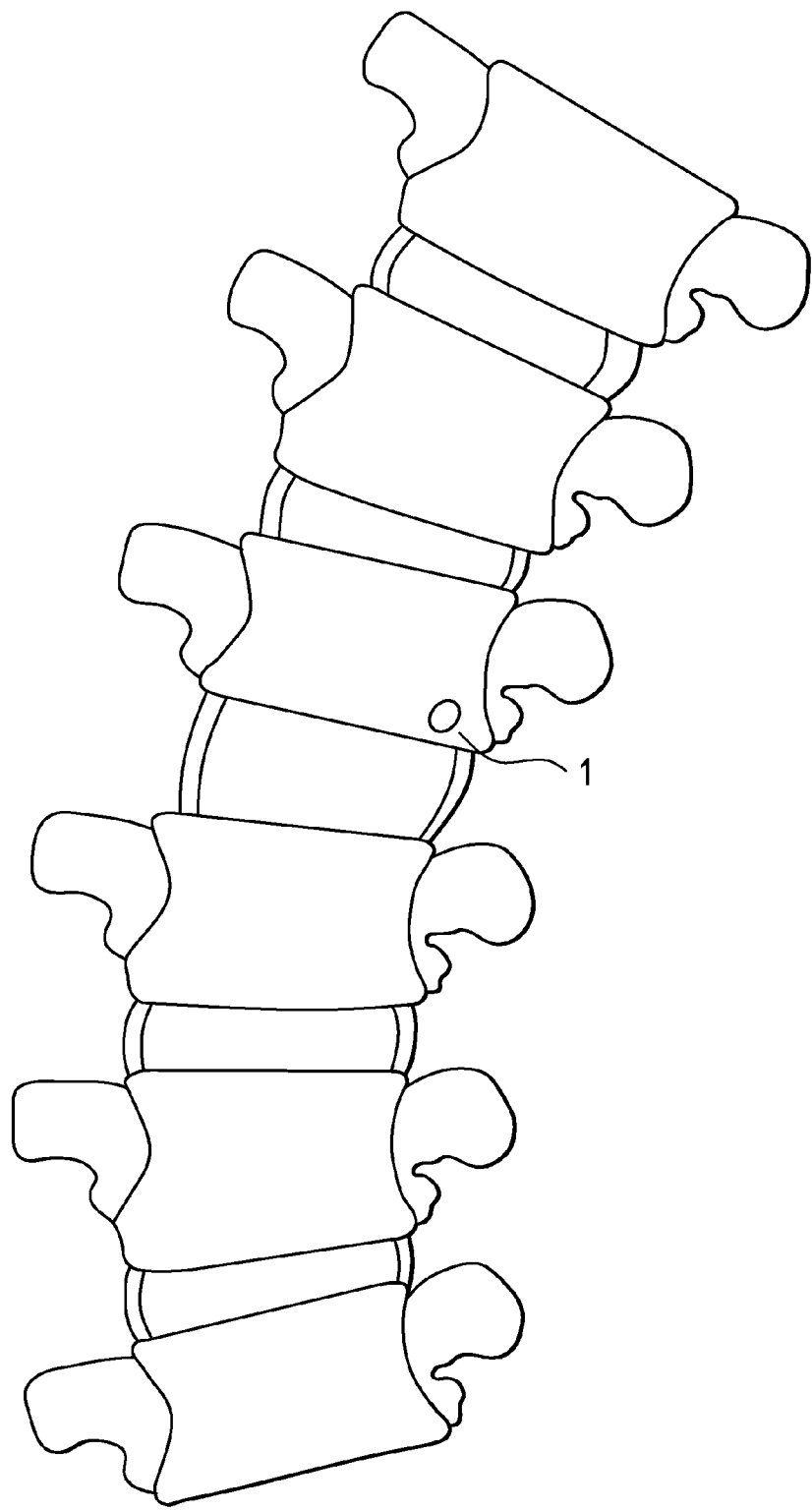
FIG. 1b is a frontal view of a human scoliotic spine, with a device of the present invention implanted in a vertebral body on the concave side of the scoliotic spine.

FIG. 1b is a frontal view of a human scoliotic spine, with a device 1 of the present invention implanted in a vertebral body on the concave side of the scoliotic spine.

The pharmaceutical of the present invention accelerates or initiates cartilage growth, preferably by either chondrocyte proliferation or chondrocyte induction. In some embodiments, the pharmaceutical is a growth factor. In some growth factor embodiments, the growth factor is a BMP (such as rhGDF-5 or OP-1), while in others, it is IGF-I.

The cannulated screws of the present invention can be inserted in an MIS approach and can be prefilled with the desired pharmaceutical. Alternatively, they can be implanted empty and designed to accept injections of formulations containing CG agents, such as BMP's (such as GDF-5), insulin-like growth factor I (IGF-I), stem cells, etc. If the reservoir within the screw becomes depleted of the injected pharmaceutical, the screw can be post-operatively re-injected with additional pharmaceutical. Preferably, the amount of pharmaceutical added post-operatively is based upon the correction level achieved by the initial elution of pharmaceutical (which may be determined by imaging).

Screws of the present invention can also be designed to allow passive micro-pumping motions via sectional modulus variations, thereby enabling self-pumping of the growth factors based upon variations in stress or strain due to patient/vertebral body movements and/or vertebral body growth expansion levels. Alternatively, the pharmaceuticals can be contained within a matrix comprising either surface-eroding or bulk-eroding resorbable polymers. These polymers provide controlled, sustained release of the pharmaceuticals from the internal reservoir of the screw as resorption takes place.

In another embodiment, growth factor release from the screw is actuated by compressing an inner mandrel onto the growth factor matrix. The inner mandrel can be a guide wire or a threaded shaft.

In another embodiment, the screw can accommodate an implantable pump that can be active over long periods.

Furthermore, if pharmaceutical-based attempts at correction via growth manipulation fail, these screws can be used to connect deformity correction rods in open or MIS procedures to fuse the spine.

Therefore, in one embodiment of the present invention, there is provided an implant assembly comprising:
  a) a pedicle screw having a distal tip, an intermediate shaft having a threaded outer surface and a longitudinal bore therethrough, a proximal head having a rod receiving region, and a pharmaceutical housed within the throughbore,
  b) a spinal rod,
wherein the spinal rod is connected to the rod receiving region.

In these instrumentation embodiments including rods, it may further be helpful to initially implant a headless screw that elutes growth factor, and then (when instrumentation is needed) attach a rod-receiving head to the screw. This full screw can now be used as above to connect to a spinal rod.

In another embodiment, the elution means of the screw is remotely activated to initiate or accelerate pharmaceutical release at the desired time and location. Remote activation means can include ultrasound, radiofrequency, light or other energy delivery means. In preferred embodiments thereof, growth factors are mixed within a matrix that is either placed or injected into the screw reservoir and the remote energy actuation excites the matrix, thereby enabling growth factor release. The matrix can comprise an energy-absorbing material, including collagen, porous polymers, resorbable polymers, nano-tubes, fibers, ceramics, hydroxyapatite, tricalcium phosphate, and calcium phosphate.

In some embodiments, the chondrogenic agent is a growth factor. As used herein, the term "growth factor" encompasses any cellular product that modulates the growth or differentiation of chondrocytes, particularly connective tissue progenitor cells. The growth factors that may be used in accordance with the present invention include, but are not limited to, members of the fibroblast growth factor family, including acidic and basic fibroblast growth factor (FGF-1 and FGF-2) and FGF-4; members of the platelet-derived growth factor (PDGF) family, including PDGF-AB, PDGF-BB and PDGF-AA; EGFs; VEGF; members of the insulin-like growth factor (IGF) family, including IGF-I and -II; the TGF-β superfamily, including TGF-β 1, 2 and 3; osteoid-inducing factor (OIF), angiogenin(s); endothelins; hepatocyte growth factor and keratinocyte growth factor; members of the bone morphogenetic proteins (BMPs) BMP-1, BMP-3, BMP-2, OP-1, BMP-2A, BMP-2B, BMP-7 and BMP-14, including MP-52 (rhGDF-5); HBGF-1 and HBGF-2; growth differentiation factors (GDFs), members of the hedgehog family of proteins, including indian, sonic and desert hedgehog; ADMP-1; and members of the colony-stimulating factor (CSF) family, including CSF-1, G-CSF, and GM-CSF; and isoforms thereof.

In some embodiments, the CG agent comprises an effective amount of a bone morphogenic protein (BMP). BMPs beneficially increasing cartilage formation by promoting the differentiation of mesenchymal stem cells (MSCs) into cartilage and/or bone.

In some embodiments, between about 1 ng and about 10 mg of a BMP are intraosseously administered into the target growth plate. In some embodiments, between about 1 µg and about 1 mg of BMP are intraosseously administered into the target growth plate.

In some embodiments, the CG agent comprises an effective amount of insulin-like growth factor I (IGF-I). IGF-I beneficially increases cartilage formation by promoting mitogenic activity and/or cell proliferation.

In one embodiment, the CG agent is a plurality of viable chondroprogenitor cells. Such viable cells, when introduced into the growth plate, have the capability of at least partially augmenting cartilage growth.

In some embodiments, these cells are obtained from another human individual (allograft), while in other embodiments, the cells are obtained from the same individual (autograft). In some embodiments, the cells are taken from cartilage tissue, while in others, the cells are taken from a non-cartilage tissue (and may, for example, be mesenchymal stem cells, or fibroblasts). In other embodiments, autograft chondrocytes (such as from the knee, hip, shoulder, finger or ear) may be used.

In one embodiment, when viable cells are selected as an additional therapeutic agent or substance, the viable cells comprise mesenchymal stem cells (MSCs). MSCs provide a special advantage for administration into a growth plate because it is believed that they can more readily survive the relatively harsh environment present in the growth plate; that they have a desirable level of plasticity; and that they have the ability to proliferate and differentiate into the desired cells.

In some embodiments, the mesenchymal stem cells are obtained from bone marrow, such as autologous bone marrow. In others, the mesenchymal stem cells are obtained from adipose tissue, preferably autologous adipose tissue.

In some embodiments, the mesenchymal stem cells injected into the growth plate are provided in an unconcentrated form, e.g., from fresh bone marrow. In others, they are provided in a concentrated form. When provided in concentrated form, they can be uncultured. Uncultured, concentrated MSCs can be readily obtained by centrifugation, filtration, or immuno-absorption. When filtration is selected, the methods disclosed in U.S. Pat. No. 6,049,026 ("Muschler"), the specification of which is incorporated herein by reference in its entirety, can be used. In some embodiments, the matrix used to filter and concentrate the MSCs is also administered into the growth plate.

The dosage of pharmaceutical administered will vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.01 to 100 milligrams per kilogram of body weight. In one embodiment, about 1.0 to 5, and sometimes about 1 to 10 milligrams per kilogram per day given in divided doses 1 to 6 times a day or in sustained release form, is effective to obtain desired results.

In some embodiments, agents can be administered in a dosage of about 0.1 to about 100 mg/kg, such as about 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20, or any combination thereof, using single or divided doses of every 24, 12, 8, 6, 4, or 2 hours, or any combination thereof. In one embodiment, the agents are administered three times in one month, e.g. three times in the first month.

In some embodiments, dosage forms (composition) suitable for internal administration generally contain from about 0.1 milligram to about 500 milligrams of active ingredient per unit. In these pharmaceutical compositions, the active ingredient will ordinarily be present in an amount of about 0.5-95% by weight based on the total weight of the composition.

In some embodiments, agents can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by commonly used techniques.

As noted above, continuous delivery of the CG agent is considered to be highly advantageous. Accordingly, in some embodiments, at least the CG agent is provided in a sustained release (i.e., delivery) device. The sustained release device is adapted to remain within the bone for a prolonged period and slowly release the CG agent contained therein to the surrounding environment and adjacent growth plate. This mode of delivery allows a CG agent to remain in therapeutically effective amounts within the growth plate for a prolonged period. One or more additional therapeutic agents can also be delivered by a sustained delivery device.

In some embodiments, the CG agent is released from the sustained delivery device predominantly by its diffusion through the sustained delivery device (which is, for example, a polymer, a porous ceramic such as hydroxyapatite, or collagen matrix such as HEALOS™). In others, the CG agent is released from the sustained delivery device predominantly by the biodegradation of the sustained delivery device. In others, the CG agent is predominantly released from the sustained delivery device by convection, such as through a drug pump housed in a bone screw.

In some embodiments, the sustained release device comprises a bioresorbable material whose gradual erosion causes the gradual release of the CG agent to the growth plate ("GP") environment. In some embodiments, the sustained release device comprises a bioresorbable polymer. In one embodiment, the bioresorbable polymer has a half-life of at least one month, for example, at least two months, e.g., at least 6 months.

In some embodiments, the sustained release device provides continuous release. In others, it provides intermittent release. Other release modes may also be used.

In some embodiments, the sustained delivery device comprises a plurality of bioerodable capsular macrospheres. In some embodiments, the CG agent is preferably contained in a gelatin (or water or other solvent) within the macrosphere capsule, and is released to the GP environment when the outer shell of the capsule has been eroded. The device can include a plurality of capsules having outer shells of varying thickness, so that the sequential breakdown of the outer shells provides periodic release of the CG agent.

In some embodiments, the sustained delivery device comprises a large plurality (e.g., at least one hundred) of water-containing chambers, each chamber containing the CG agent. Each chamber is defined by bilayer lipid membranes comprising synthetic duplicates of naturally occurring lipids. The release of the drug can be controlled by varying at least one of the aqueous excipients, the lipid components, and the manufacturing parameters. In one embodiment, the formulation comprises no more than 10% lipid. In some embodiments, the DEPOFOAM™ technology of Skyepharma PLC (London, United Kingdom) is selected.

In some embodiments, the sustained delivery device comprises a delivery system disclosed in U.S. Pat. No. 5,270,300

("Hunziker"), the specification of which is incorporated herein by reference in its entirety.

In some embodiments, the sustained delivery device comprises a liposomal delivery system, such as that disclosed in WO 03/000190. Liposomes are small spheres whose walls are layers of lipids with water. As they form, liposomes entrap water and any water soluble solutes that are present. Because of this entrapping ability, they are useful as delivery systems. For the purposes of the present invention, a preferred embodiment includes the use of a multilamellar vesicle, and any naturally occurring phospholipid, such as dipalmitoylphosphatidylcholine (DPPC).

A liposome may be a vesicle having at least one lipid bilayer surrounding an inner liquid phase (a lipid bilayer surrounding either a liquid core or a liquid phase dispersed between it and another lipid bilayer). The liposome may have various structures such as multilamellar (MLVs), unilamellar (ULVs) and paucilamellar (PLVs) vesicles. The resulting structure of the liposome is dependent, in part, on the choice of materials forming the hydrophobic phase and the manufacturing parameters, such as temperature and incubation time.

Some liposomes comprise at least one amphiphilic bilayer-forming substance. The therapeutic substances contained therein may be contained either within the lipid bilayer or the hydrophilic compartments of the liposome. The amphiphilic bilayer-forming substance comprises both a hydrophilic and a lipophilic group and is capable of forming, either alone or in combination with other lipids, the bilayer of a liposome. The lipid can have single or multiple lipophilic side chains being either saturated or unsaturated in nature and branched or linear in structure. The amphiphilic bilayer-forming substance can be a phosphoholipid or a ceramide.

In some embodiments, the sustained delivery device comprises the co-polymer poly-DL-lactide-co-glycolide (PLG). Preferably, the formulation is manufactured by combining the CG agent, the co-polymer and a solvent to form a droplet, and then evaporating the solvent to form a microsphere. The plurality of microspheres are then combined in a biocompatible diluent. Preferably, the CG agent is released from the co-polymer by its diffusion therethrough and by the biodegradation of the co-polymer. In some embodiments hereof, the PROLEASE® technology of Alkermes (Cambridge, Mass.) is selected.

In some embodiments, the sustained delivery device comprises a hydrogel. Hydrogels can also be used to deliver the CG agent in a time-release manner to the GP environment. A "hydrogel" is a substance formed when an organic polymer (natural or synthetic) is set or solidified to create a three-dimensional open-lattice structure that entraps molecules of water or other solution to form a gel. The solidification can occur, e.g., by aggregation, coagulation, hydrophobic interactions, or cross-linking. The hydrogels employed in this invention rapidly solidify to keep the CG agent at the application site, thereby eliminating undesired migration from the GP. The hydrogels are also biocompatible with, e.g., not toxic to, cells suspended in the hydrogel.

A "hydrogel-CG agent composition" is a suspension of a hydrogel-containing desired agent. The hydrogel-CG agent composition forms a uniform distribution of CG agent with a well-defined and precisely controllable density. Moreover, the hydrogel can support very large densities of CG agent.

Hydrogels suitable for use in the present invention include water-containing gels, i.e., polymers characterized by hydrophilicity and insolubility in water. See, for instance, "Hydrogels", In Concise Encyclopedia of Polymer Science and Engineering, Mark et al., eds. (Wiley and Sons) pp. 458-459 (1990), the disclosure of which is incorporated herein by reference in its entirety. Although their use is optional in the present invention, the inclusion of hydrogels can be highly advantageous since they tend to contribute a number of desirable qualities. By virtue of their hydrophilic, water-containing nature, hydrogels can:

a) house viable cells, such as mesenchymal stem cells and
b) assist with load bearing capabilities of the cartilage.

In one embodiment, the hydrogel is a fine, powdery synthetic hydrogel. The hydrogel can include one or more of the following: polysaccharides, proteins, polyphosphazenes, poly(oxyethylene)-poly(oxypropylene) block polymers, poly(oxyethylene)-poly(oxypropylene) block polymers of ethylene diamine, poly(acrylic acids), poly(methacrylic acids), copolymers of acrylic acid and methacrylic acid, poly(vinyl acetate), and sulfonated polymers.

In general, these polymers are at least partially soluble in aqueous solutions, e.g., water, or aqueous alcohol solutions that have charged side groups, or a monovalent ionic salt thereof. There are many examples of polymers with acidic side groups that can be reacted with cations, e.g., poly(phosphazenes), poly(acrylic acids), and poly(methacrylic acids). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine) and poly(vinyl imidazole).

In some embodiments, the sustained delivery device includes a polymer selected from the group consisting of PLA, PGA, PCL and mixtures thereof.

When the sustained delivery vehicle is essentially a depot, preferably, the formulation of the present invention is injected into or adjacent the GP through a small bore needle. In some embodiments, the needle has a bore of about 22 gauge or less, so that the possibilities of producing tissue damage are mitigated. For example, the needle can have a bore of about 24 gauge or a smaller bore, so that the possibilities of producing tissue damage are even further mitigated.

In some embodiments, the formulation comprises a suitable biocompatible solvent such as saline. In some embodiments, the solvent is selected from the solvents disclosed in U.S. Pat. No. 6,277,969, the specification of which is incorporated herein by reference in its entirety. In some embodiments, the solvent is preferably selected from the group consisting of dimethyl sulfoxide (DMSO) and ethanol.

Figure 2:
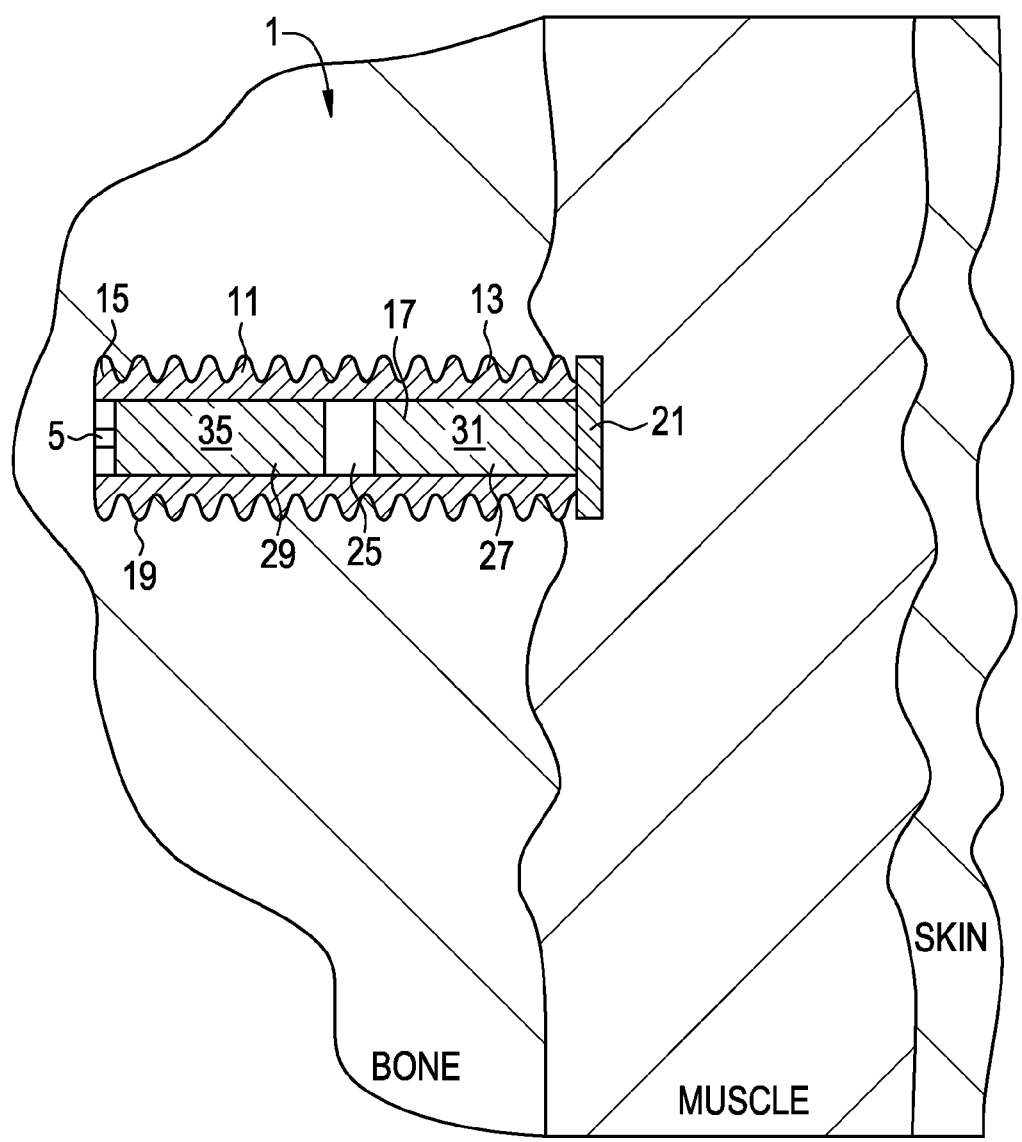
FIG. 2 is a cross-section of an osmotic drug pump implant of the present invention.

Now referring to FIG. 2, there is provided an osmotic pump implant 1 for providing sustained delivery of a therapeutic agent into a GP. In this embodiment, the osmotic pump implant comprises:

a) a tubular member 11 including a proximal end portion 13, a distal end portion 15 and a throughbore 17,
b) a semi-permeable membrane 21 located in the proximal end portion of the tubular member,
c) a piston 25 provided in the tubular member, defining a proximal chamber 27 and a distal chamber 29,
d) an osmotic engine 31 located in the proximal chamber, and
e) a therapeutic drug 35 located in the distal chamber, wherein the tubular member has an outer surface adapted to anchor to the bone, for example, an outer surface having a fastening means 19 (e.g., a threadform) thereon.

The device shown in FIG. 2 works upon the following principle. Water infiltrates the semi-permeable membrane and is imbibed in the osmotic engine. Upon the receipt of water, the material selected for the osmotic engine swells. Since the semi-permeable membrane is fixed and the piston is axially movable, the force produced by the swelling of the osmotic engine forces the piston to slide distally. This movement in turn forces the drug out the distal exit port 5. In some embodiments, design features of the device are adopted from U.S. Pat. No. 5,728,396 ("Peery"), the specification of which is incorporated by reference in its entirety.

In preferred embodiments, the therapeutic drug provided in FIG. 2 is a CG agent. In some embodiments, the device is tailored to provide the CG agent in an amount of at least 70% of the predetermined therapeutic level for at least about six (6) months.

A major impediment to many osmotic engine-based delivery devices is the start-up time to delivery. In effect, the osmotic engine should be primed before the therapeutic drug is eluted from the distal end of the device.

Because the bone is a very vascular tissue, it may be that the vascularity also drains the locally administered CG agent from the GP region very quickly. For example, it is reasonable to expect CG agent levels to be essentially depleted from the bone within about 10-15 days of their local administration. Since in the case of many CG agents, it may be advantageous to provide an effective amount of the CG agent within the GP for a longer duration, there appears to be a need for a device that insures the continuous presence of the CG agent for an indefinite period.

Although the device of FIG. 1a is useful for delivering a CG agent for a period of at least 6 months, the requirement that the CG agent be delivered ad infinitum may require replacement of the device of FIG. 1a with another similar device. However, it is believed that replacement of the device of FIG. 1a will be problematic for at least two reasons. First, removal of the device (for example, by turning the threadform in the opposite direction) may well damage the bone surrounding the device. This damage may produce a loose fit between the bone and the second device when it is ultimately inserted into the bone. Second, the threadform may have been osteointegrated into the bone, thereby making its removal extremely difficult.

Accordingly, there is a need for a device that allows for easy removal of the drug pump.

Figure 3:
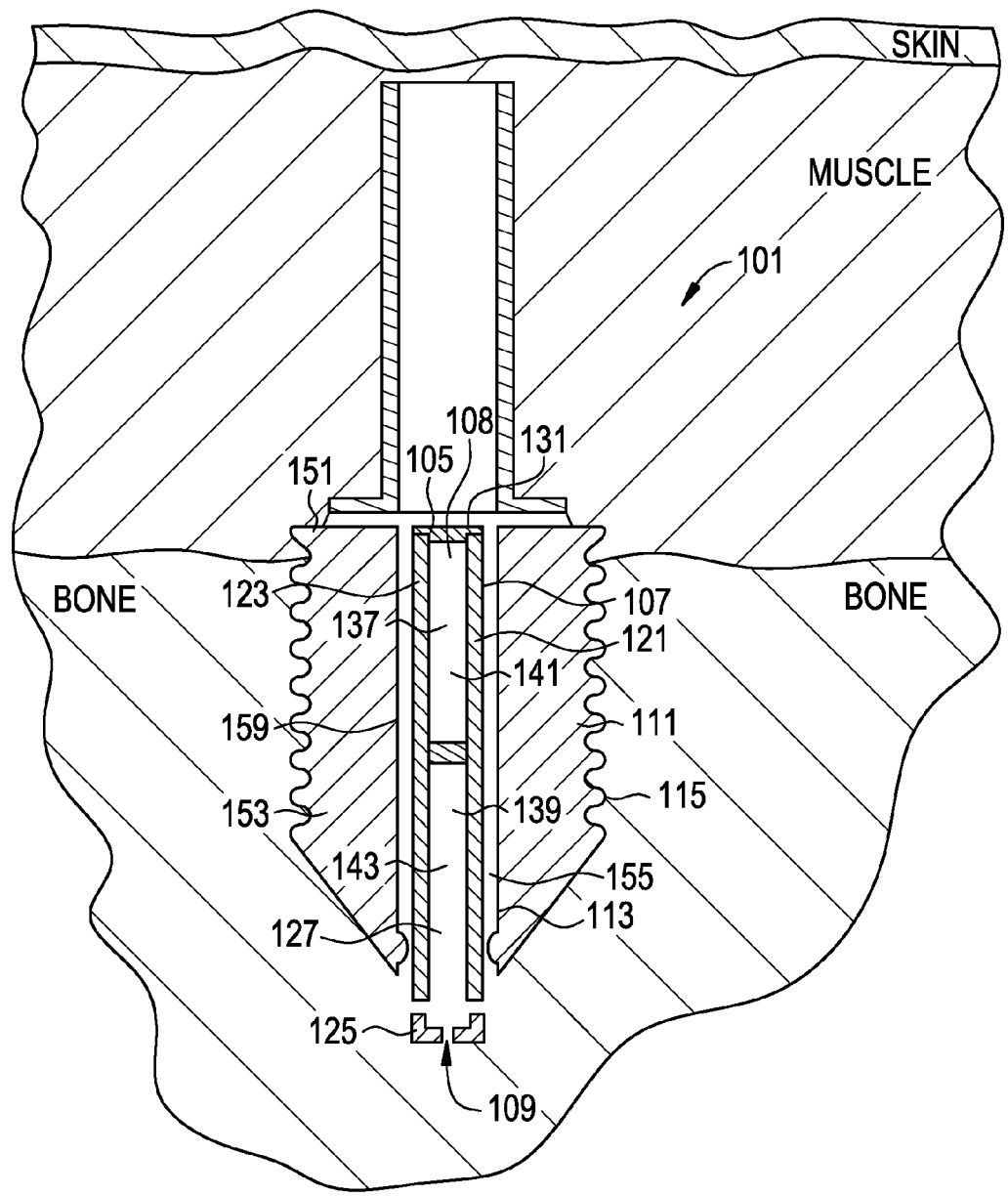
FIG. 3 is a cross-section of a modular drug delivery device of the present invention.

For example, now referring to FIG. 3, there is provided a drug delivery implant 101 for providing sustained delivery of a therapeutic agent to a bone, comprising:
  a) an osmotic pump 105 having an outer surface 107, an inner chamber 108 and an exit port 109, and
  b) a carrier 111 having a recess 113 for receiving the osmotic pump and a means for fastening to bone 115.
The drug delivery implant of the present invention is advantageous because it allows for the intermittent removal and replacement of a spent osmotic pump without harming the surrounding bone.
In some embodiments, the osmotic pump comprises:
  a) a tubular member (i.e., tube) 121 including a proximal end portion 123, a distal end portion 125 and a throughbore 127,
  b) a semi-permeable membrane 131 located in the proximal end portion of the tubular member,
  c) a piston 135 provided in the tubular member, defining a proximal chamber 137 and a distal chamber 139,
  d) an osmotic engine 141 located in the proximal chamber, and
  e) a chondrogenic therapeutic drug 143 located in the distal chamber.
In some embodiments, the carrier 111 comprises a tubular member comprising:
  i) proximal end portion 151,
  ii) a distal end portion 153 and
  iii) a throughbore 155 defining an inner surface 159, wherein the outer surface has a threadform 115 thereon and the inner surface is adapted for releasable engagement of the outer surface of the osmotic pump.

In some embodiments, the implant comprises a throughbore in fluid communication with the exit port which can be oriented within the vertebral body to release the CG agent to the targeted location. In some embodiments, the drug pump comprises an osmotic engine disposed within the throughbore. In some embodiments, the drug pump contains a formulation (e.g., a first formulation) comprising an effective amount of a CG agent. In some embodiments, the drug pump comprises a cylindrical outer surface, the carrier has a throughbore and the cylindrical outer surface is adapted to fit within the throughbore.

In use, the device is implanted into the bone and the first osmotic pump is actuated and provides therapeutic amounts of chondrogenic drug to the patient. After the first osmotic pump is spent, it is removed and replaced by a second fresh osmotic pump. This process can be continued indefinitely.

When a modular drug delivery device is selected, the system should be designed so that the drug pump is easily insertable into the carrier, remains in place during use and is easily removable.

Figure 4:
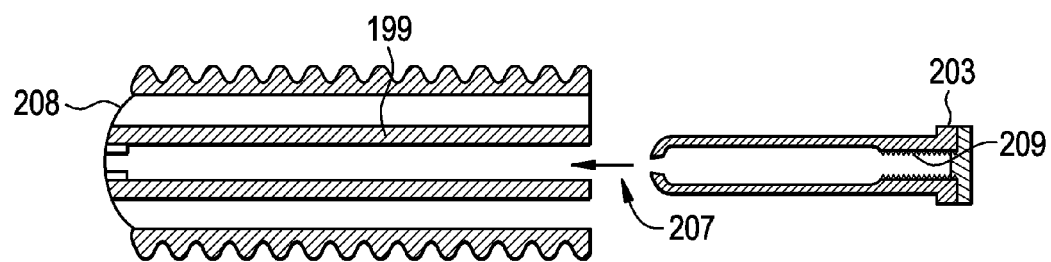
FIG. 4 is a cross-section of another embodiment of a modular drug delivery device of the present invention.

In some embodiments (for example, as shown in FIG. 4), these attributes are achieved by providing a rubber annulus 199 upon the inner annulus of the drug pump bore.

Figure 5:
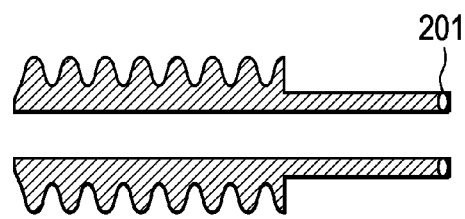
FIG. 5 is a cross-section of a carrier of the present invention having radio-opaque markers.

Now referring to FIG. 5, in some embodiments, the proximal portion of the flexible tube is provided with a radio-opaque marker 201 (See FIG. 14) so that its identification under fluoroscopy is even easier. In other embodiments, the radio-opaque marker(s) are replaced with LEDs.

Figure 6:
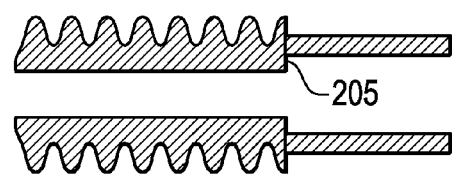
FIG. 6 is a cross-section of a carrier of the present invention having a stop for preventing over-insertion of the drug pump.

Now referring to FIGS. 4 and 6, in some embodiments, the pump has a proximal laterally extending ridge 203, and the carrier has a ledge 205. Together, these features provide a stop that insures the drug pump is not over-extended into the carrier. When a replacement drug pump is provided in the carrier, it would be advantageous to insure the ultimate location of the pump vis-a-vis the carrier. Accordingly, in some embodiments, the drug pump is provided with a stop. In some embodiments, the stop comprises a lip extending radially from the outer surface of the proximal end portion of the pump. When the replacement pump is inserted into the carrier bore, the stop will seat upon a ledge formed upon the proximal end of the annulus, thereby insuring a fixed location within the carrier.

In some embodiments, the barrel of the osmotic pump is made of a titanium alloy.

In some embodiments, the carrier is made of a titanium alloy or carbon-fiber reinforced polymer, such as PEEK. Preferably, it is made of a material having a stiffness relatively close to that of cancellous bone. Preferably, it is made of a material having a stiffness (i.e., a modulus of elasticity) of between about 0.1 and about 10 GPa.

In some embodiments, the exit port holes at the distal end portion of the osmotic pump are coated with a non-stick material, such as TEFLON®. It is believed that the TEFLON® will prevent bony ingrowth into the exit port holes from the bony tissue outside.

In some embodiments of the present invention, in addition to applying the CG agent to the concave side of the deformity, a second pharmaceutical (that retards chondrogenesis) is applied to the convex side of the deformity. In some embodiments, this second pharmaceutical is selected from the group consisting of a cross-linking agent, a steroid.

In some embodiments, the eluting fenestrations of the screw are aligned along the longitudinal axis of the screw and are oriented by the surgeon towards one of the targeted growth plates (as in FIG. 1a). This provides for direction elution of the CG agent, thereby making the CG agent more effective.

Example I

This non-limiting prophetic example describes how to administer intraosseously a formulation comprising a CG agent into a growth plate.

First, the clinician provides a local anesthetic (such as 5 ml lidocaine) to the region dorsal to the vertebral body to reduce subcutaneous pain.

Next, the clinician punctures the skin of the patient dorsal to the bone with a relatively large (e.g., 18-19 gauge) needle having a stylet therein, and advances the needle through subcutaneous fat and dorsal sacrolumbar ligament and muscles to the outer edge of the bone, and finally punctures the cortical wall of the bone.

Next, the stylet and needle are advanced about 7 mm, and then removed thereby leaving a tubular recess in the bone.

Figure 7A:
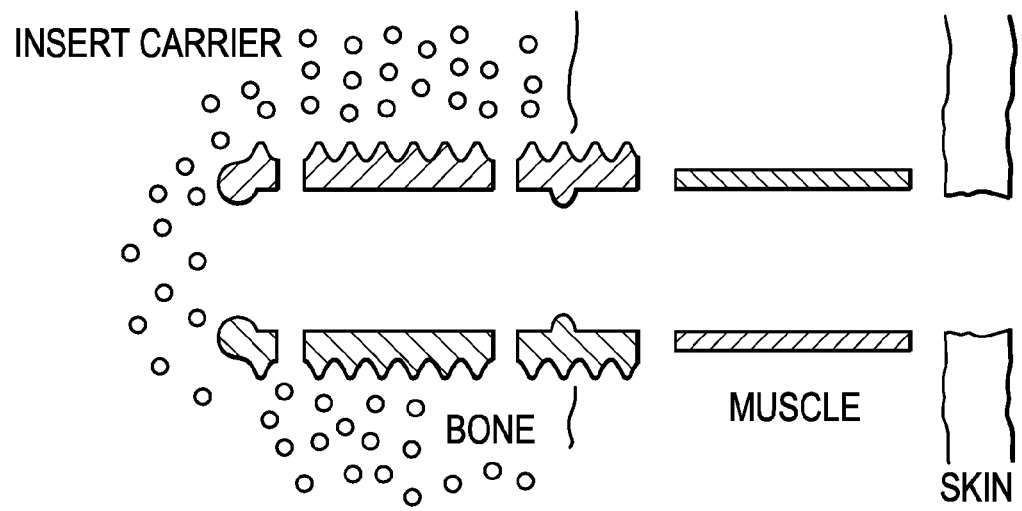
FIGS. 7a and 7b are cross-sections of a method of using a device of the present invention to treat a growth plate.

Next, now referring to FIG. 7a, a threaded carrier having an inner throughbore and a plurality of exit holes is inserted into the recess by screwing the thread form into the tubular recess.

Figure 7B:
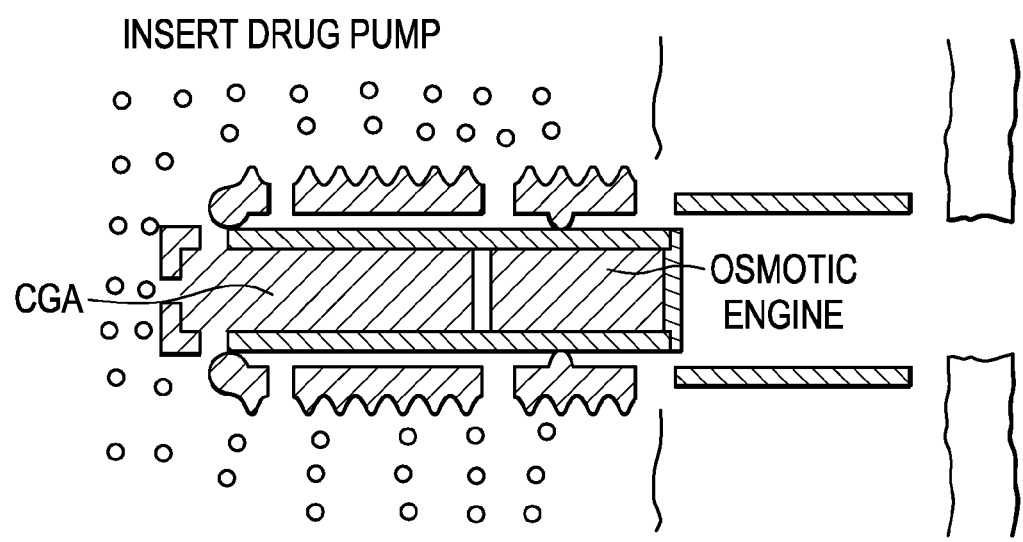

Now referring to FIG. 7b, an osmotic drug pump is snugly placed into the throughbore of the carrier. The drug pump contains a first distally located formulation comprising a CG agent (such as a BMP or IGF-I).

As water infiltrates the semi-permeable membrane of the osmotic pump, the osmotic engine expands thereby, forcing each formulation distally. The first bone forming agent exits through each of the three distal holes.

While this invention has been particularly shown and described with references to preferred embodiments thereof, it will be understood by those skilled in the art that various changes in form and details may be made therein without departing from the scope of the invention encompassed by the appended claims.

CIP

Just as the above embodiments treat spinal deformities such as scoliotic curves by accelerating bone growth on the concave side of the scoliotic vertebral body, it is believed that benefit to the patient can also be realized by inhibiting bone growth on the convex side of the vertebral body alone, or in conjunction with accelerating growth on the concave side. This can be achieved by effecting local elution of a bone growth inhibitor on the convex side of the scoliotic vertebral body in the area of the growth plate.

In one embodiment, the bone growth inhibitor is a cycline compound, such as tetracycline. It has been reported that chronic oral administration of tetracycline to young patients results in a significant inhibition of bone growth. For example, Cohlan, Am. J. Dis. Child., 105, 453, 1963, reported a 40% inhibition of the fibular growth rate in premature babies who had been given about 100 mg/kg/day of tetracycline for about 9-12 days.

Demers, Can. Med. Assn. J., vol. 99, Nov. 2, 1968, pp. 849-854, reports that there appear to be three theories that could explain the inhibition of bone growth by tetracycline. These are the formation of a calcium-tetracycline complex (chelation), inhibition of protein synthesis and inhibition of enzymes essential to growth.

Simmons, Clin. Orthop. Rel. Res., 1983 examined the effect of a one year course of 50 mg/kg/day tetracycline treatment on the bone growth and maturation in adult female rhesus monkeys. Simmons found that while the treated group possessed normal concentration of bone minerals such as calcium, inorganic phosphorous and hydroxyproline, the percentage of highly mineralized osteons labeled with tetracycline was subnormal in the treated group. In addition, the treated group also displayed abnormally high Ca/Pi ratios in the temporally young newly formed bone mineral. Simmons concluded that protracted, high dose tetracycline treatment impairs bone growth and maturation even in adult primates.

Without wishing to be tied to a theory, it is believed that tetracycline may impact the growth of bone by binding to osteoid, which is newly formed bone. It is further believed that the deposition of a layer of tetracycline upon an osteoid surface effectively inhibits the deposition of additional osteoid upon the initial osteoid surface.

Because the proposed growth inhibition is locally applied (i.e., limited to one or two levels in the spine), it is believed that the overall height of the patient will be only minimally affected, as the growth rate of only one or two vertebral bodies will be impacted while the remainder of the vertebral bodies will be free to grow at natural, bilaterally equal rates.

Because the administration of tetracycline in accordance with the present invention will be local, it is believed that the practice of the present invention will have a negligible systemic effect on the patient. However, if there is concern for the antibiotic nature of tetracycline, then tetracycline analogs having reduced antibiotic potency (such as CMT) may replace tetracycline in the practice of the present invention.

In some embodiments, a tetracycline analog possessing only the A ring of tetracycline is selected. It has been reported that such analogs possess up to about 50% of the bone-binding ability of tetracycline.

Since a vertebral body is approximately $1/100$ the weight of the human body, and a child is about 30 kg, it may be desirable for the implant to elute about 30 mg of tetracycline per day in order to reach the 100 mg/kg/day value reported in the literature for significant bone growth inhibition. Since the solubility of tetracycline.HCl in water is about 100 mg/ml, the implant would need to deliver about $1/3$ ml of fluid each day. This may entail weekly refills of the implant.

In some embodiments, the cycline compound is selected from the group consisting of chlortetracycline, demethylchlortetracycline, doxycycline, lymecycline, oxicycline, oxytetracycline, demeclocycline, meclocycline, methacycline, roliteracycline, tetracycline, minocycline, chemically modified tetracycline (CMT) and KB-R7785. Preferably, tetracycline, doxycycline or minocycline is selected. Most preferably, tetracycline is selected.

Therefore, in accordance with the present invention, there is provided a method of correcting spinal deformity comprising the steps of:
 a) locating a cycline-loaded implant adjacent to a targeted spinal growth plate in a patient having a spinal deformity, and
 b) eluting the cycline onto the growth plate in an amount effective to retard bone growth in the targeted spinal growth plate,
wherein the implant is at least partially located in a pedicle, and
wherein the cycline is substantially eluted onto the growth plate on a convex side of the spinal deformity.

In some embodiments, the tetracycline is injected adjacent the growth plate on a convex side of the spinal deformity in the form of a sustained release device. In some embodiments, the sustained release device comprises a cycline compound and a bioresorbable material whose gradual erosion causes the gradual release of the tetracycline to the growth plate ("GP") environment. In some embodiments, the sustained release device comprises a cycline compound and a bioresorbable polymer. In one embodiment, the bioresorbable polymer has a half-life of at least one month, for example, at least two months, e.g., at least 6 months. In such embodiments, a needle can be delivered down the pertinent pedicle and injections provided therethrough on a periodic basis.

Therefore, in accordance with the present invention, there is provided a method of correcting spinal deformity comprising the steps of:
a) injecting a cycline-loaded implant comprising a sustained release device adjacent to a targeted spinal growth plate in a patient having a spinal deformity, so that the cycline is substantially eluted from the sustained release device onto the growth plate on a convex side of the spinal deformity.

We claim:

1. A method of correcting spinal deformity comprising the steps of:
a) locating a cycline-loaded implant adjacent to a spinal growth plate in a patient having a scoliotic spinal deformity, and
b) eluting the cycline onto the growth plate in an amount effective to retard bone growth in the spinal growth plate,
wherein the implant has a distal exit port adapted for eluting a cycline, and
wherein the distal exit port is located in a vertebral body,
wherein the cycline is substantially eluted onto the growth plate on a convex side of the spinal deformity,
wherein the implant comprises a cannulated bone screw, and
wherein the screw is remotely activated to initiate or accelerate cycline elution at a desired time and location.

2. The method of claim 1 wherein the bone screw has a cannulated internal reservoir that contains the cycline.

3. The method of claim 2 wherein the bone screw has a shaft comprising an outer surface and fenestrations, the fenestrations providing fluid connection between the reservoir and the outer surface and allowing the cycline to elute therethrough.

4. The method of claim 3 wherein cycline release from the screw is actuated by compressing an inner mandrel onto a matrix comprising the cycline.

5. The method of claim 4 wherein the inner mandrel is a guide wire or a threaded shaft.

6. The method of claim 3 wherein the reservoir contains a pump.

7. The method of claim 1 wherein the screws allows passive micro pumping motions via sectional modulus variations, thereby enabling self pumping of the cycline based upon stress or strain from either patient movements, vertebral body movements, or vertebral body growth expansion levels.

8. The method of claim 1 wherein the bone screw is threaded.

9. The method of claim 1 wherein the bone screw is unthreaded.

10. The method of claim 1 wherein the cycline is tetracycline.

11. The method of claim 10 wherein the cycline is a tetracycline analog.

12. The method of claim 10 wherein the cycline is contained within a matrix comprised of either a surface-eroding or a bulk-eroding resorbable polymer.

13. The method of claim 1 wherein the cycline consists essentially of the A ring of tetracycline.

14. The method of claim 1 further comprising the step of:
c) refilling the reservoir with the cycline.

15. The method of claim 14 wherein the refilling is accomplished after an assessment of spinal correction due to cycline elution.

16. The method of claim 1 further comprising the step of:
c) attaching the screw to a correction rod.

17. The method of claim 1 wherein the remote activation is accomplished by energy delivery.

18. The method of claim 17 wherein the energy is selected from the group consisting of ultrasound, radiofrequency, and light.

19. The method of claim 17 wherein the pharmaceutical is located within a matrix that is located within the screw, and the remote delivery of energy excites the matrix, enabling cycline release.

20. The method of claim 19 wherein the matrix comprises an energy absorbing material.

21. The method of claim 20 wherein the energy absorbing material is selected from the group consisting of collagen, a porous polymer, a resorbable polymer, a nano-tube, and a fiber.

22. The method of claim 1 wherein the implant is at least partially located in a pedicle.

* * * * *